US012663407B2

(12) United States Patent
Renfro

(10) Patent No.: US 12,663,407 B2
(45) Date of Patent: Jun. 23, 2026

(54) DETERMINING PROPERTIES OF LIQUIDS WITHIN A SEALED CONTAINER

(71) Applicant: University of Kentucky Research Foundation, Lexington, KY (US)

(72) Inventor: Michael W. Renfro, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 75 days.

(21) Appl. No.: 18/775,558

(22) Filed: Jul. 17, 2024

(65) Prior Publication Data

US 2025/0027926 A1     Jan. 23, 2025

Related U.S. Application Data

(60) Provisional application No. 63/527,175, filed on Jul. 17, 2023.

(51) Int. Cl.
*G01N 33/14* (2006.01)
*G01N 21/84* (2006.01)

(52) U.S. Cl.
CPC ........... *G01N 33/146* (2013.01); *G01N 21/84* (2013.01); *G01N 2021/8405* (2013.01); *G01N 2201/088* (2013.01)

(58) Field of Classification Search
CPC ................. G01N 33/146; G01N 21/84; G01N 2021/8405; G01N 2201/088; G01N 21/8507; G01N 2021/8528

USPC .......................................................... 356/477
See application file for complete search history.

(56) References Cited

U.S. PATENT DOCUMENTS

| | | | |
|---|---|---|---|
| 11,793,940 B2 * | 10/2023 | Klemm | A61M 5/24 |
| 2015/0146201 A1 * | 5/2015 | Burka | G01J 3/44 |
| | | | 356/301 |

OTHER PUBLICATIONS

Reissued Patent No. 9,175 to Frederick Stitzel for "Rack for Tiering Barrels," Apr. 27, 1880.
Rathinam, M., L.R. Petzold, "A New Look at Proper Orthogonal Decomposition," SIAM J. Numer. Anal. 41 (2003) 1893-1925.
Kim, H.N., M.P. Hawron, W. Hassan, E.H. Jordan, M.W. Renfro, "Contaminant identification during laser cleaning of thermal barrier coatings," Surface & Coatings Tech. 270 (2015) 86-94.

* cited by examiner

*Primary Examiner* — Md M Rahman
(74) *Attorney, Agent, or Firm* — Stites & Harbison PLLC; Mandy Wilson Decker

(57) ABSTRACT

Devices, systems, and methods for measuring properties of liquids or surrounding gasses within a sealed container. Some embodiments of the devices, systems, and methods disclosed herein are useful for determining and monitoring alcohol (ethanol) content of a liquid within a sealed container. Some embodiments are also useful for determining and monitoring additional properties of the liquid within the sealed container, such as liquid depth (volume) and/or presence of trace chemicals and flavor components.

14 Claims, 9 Drawing Sheets

DETERMINING PROPERTIES OF LIQUIDS WITHIN A SEALED CONTAINER

RELATED APPLICATIONS

This application claims priority from U.S. Provisional Application Ser. No. 63/527,175 filed Jul. 17, 2023, the entire disclosure of which is incorporated herein by this reference.

TECHNICAL FIELD

The present disclosure is directed to devices, systems, and methods for measuring properties of liquids. In particular, the disclosure is directed to devices, systems, and methods for optically measuring properties of liquids or surrounding gasses within a sealed container. Some embodiments of the devices, systems, and methods disclosed herein are useful for determining and monitoring alcohol (ethanol) content of a liquid within a sealed container. Some embodiments of the devices, systems, and methods disclosed herein are also useful for determining and monitoring additional properties of the liquid within the sealed container, such as liquid depth (volume) and/or presence of trace chemicals and flavor components.

INTRODUCTION

Production of a number of alcoholic beverages involves an aging process that takes place in a sealed container, such as a barrel. Examples of such alcoholic products include whiskey/whisky, including American whiskey, bourbon, rye, scotch, Irish Whiskey, Scottish whisky, Canadian whisky, Japanese whisky, brandy, including cognac, Armagnac, Spanish brandy, rum, tequila, mescal, calvados, pisco, wine, beer, cider, mead, and sake.

When producing an aged alcoholic beverage, measuring the alcohol by volume (ABV) during the aging process is important for a number reasons. ABV indicates the percentage of ethanol (alcohol) present in the total volume of the liquid. Monitoring ABV allows for consistent product quality assessment, allowing for compliance with desired product standards and with regulatory standards, which provide specific ABV levels for labeling and taxation purposes. For example, bourbon is typically distilled to no more than 80% ABV (160 proof), entered into the barrel for aging at no more than 62.5% ABV (125 proof), and bottled at a minimum of 40% ABV (80 proof).

Monitoring ABV also helps in understanding the interaction between the beverage and the barrel or container, as the alcohol content can fluctuate due to factors like absorption into the wood and evaporation (known as the "angel's share"). These data can provide valuable insights into optimizing the aging process to achieve desired flavor profiles and characteristics. Additionally, accurate ABV measurements can enhance the efficiency of the production process by allowing producers to make informed adjustments in real-time, reducing waste and ensuring that the final product meets the desired specifications before bottling and distribution.

Unfortunately, known devices, systems, and methods for measuring ABV are unsuitable for monitoring an aging liquid within a sealed container.

Hydrometer-based methods are known for use in measuring ABV. A hydrometer measures the specific gravity (SG) of a liquid before and after fermentation. The difference in SG readings is used to calculate the alcohol content. While such methods have been used in the context of aged alcoholic beverages, it requires breaching the seal of the aging container to perform sampling, and is therefore unusable for aging methods that rely on strict maintenance of the seal of the aging container. Additional shortcomings of this method include accuracy being impacted by temperature variations of the samples, and it has also been found to be less accurate for high-alcohol-content liquids (i.e., liquids above about 40% ABV).

Another method for measuring ABV of a liquid involves use of a refractometer, which measures the refractive index of a liquid. The refractive index changes with sugar and alcohol content, allowing ABV to be calculated. Such methods are also unsuitable for use with sealed aging containers because sampling is required. Additionally, use of a refractometer often requires correction formulas to calculate ABV because alcohol and sugar affect refractive index differently. Such methods are also less accurate for high-alcohol-content liquids.

Gas chromatography (GC) is another method that can be used to assess ABV. GC separates and measures volatile compounds, such as alcohol, in a liquid. A small sample is vaporized and injected into a chromatograph, and the alcohol content is measured by analyzing elution times and peak areas. Yet again, this method requires sampling, making it unsuitable for use with sealed aging containers. The results can also be time-consuming to obtain and complex to analyze.

Another method for measuring ABV of a liquid involves use of infrared spectroscopy or near-infrared (NIR) spectroscopy, which can be used to measure the absorption of IR and/or NIR light, which can provide information about molecular composition of a liquid, including alcohol content. IR and/or NIR light is passed through a sample of the liquid, and the absorption spectrum is analyzed to determine alcohol content. However, known methods of IR and NIR spectroscopy are unsuitable for use with sealed aging containers because sampling is required.

Additional options for measuring ABV can make use of a digital density meter or nuclear magnetic resonance (NMR) spectroscopy; however, these known methods are also unsuitable for use with sealed aging containers because of the need to obtain a sample.

Accordingly, there remains a need in the art for devices, systems, and methods for accurately monitoring an aging liquid within a sealed container.

SUMMARY

The presently-disclosed subject matter meets some or all of the above-identified needs, as will become evident to those of ordinary skill in the art after a study of information provided in this document.

This Summary describes several embodiments of the presently-disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this Summary or not. To avoid excessive repetition, this Summary does not list or suggest all possible combinations of such features.

The presently-disclosed subject matter includes devices, systems, and methods for conducting optical measurements of a liquid in a sealed container. As will be appreciated by one of ordinary skill in the art upon study of this document, such devices, systems, and methods can be useful for monitoring an alcoholic beverage being aged in a sealed container, or for other applications. When used for monitoring an alcoholic beverage being aged, monitoring can include detecting properties such as alcohol by volume (ABV) (%), liquid height (volume) in the container, presence of trace chemicals and flavor components, and other physical and environmental properties of the liquid and internal environment of the sealed container.

In some embodiments of the presently-disclosed subject matter a device is provided for conducting optical measurements of a liquid in a sealed container. The device can include a probe with fiber optic or light guiding capabilities having a leg extending downward through a bung and having an end at an upper terminus of the leg that extends upward through the bung. The leg can optionally include a series of crimps, such that its diameter shrinks and expands across its length. A fiber optic connector can be included for detachably coupling the end of the probe to a light source and/or a measurement system.

In some embodiments of the device, the probe is substantially U-shaped, having the leg extending downward, a base curving back up, and a second leg extending upward. The end at the upper terminus of the first leg and the end at the upper terminus of the second leg both extend through the bung. The probe can also include a second fiber optic connector for detachably coupling the second end of the probe to a light source and/or a measurement system.

In some embodiments, the device also includes a sealed container, wherein the bung is placed such that the legs and base of the probe extend into the sealed container, and the fiber optic connectors are accessible on the outside of the sealed container.

In some embodiments, the device includes a protective sleeve surrounding the probe.

In some embodiments of the presently-disclosed subject matter a system is provided for conducting optical measurements of a liquid in a sealed container, which includes a device including a probe with fiber optic or light guiding capabilities having a leg extending downward through a bung; and an end at an upper terminus of the leg that extends upward through the bung; and a fiber optic connector for detachably coupling the end of the probe to a light source and/or a measurement system, a sealed container, wherein the bung is placed such that the probe extends into the sealed container, and the fiber optic connector is accessible on the outside of the sealed container, a light source, and a measurement system. In some embodiments of the system, the leg of the probe includes a series of crimps, such that its diameter shrinks and expands across its length.

In some embodiments of the system, the probe is substantially U-shaped, having the leg extending downward, a base curving back up, and a second leg extending upward, wherein the end at the terminus of the first leg and a second end at the terminus of the second leg both extend upward through the bung, and a second fiber optic connector for detachably coupling the second end of the probe to a light source and/or a measurement system.

In some embodiments of the system, the light source emits light having wavelengths of about 400 nm to about 6000 nm, about 400 nm to about 2500 nm, or about 3000 nm to about 6000 nm.

In some embodiments of the system, the measurement system is a spectrometer or photodetector. In some embodiments of the system, the measurement system detects light having wavelengths of about 400 nm to about 6000 nm, about 900 nm to about 1700 nm, about 1100 nm to about 1600 nm, 1300 to about 1400 nm or about 3000 nm to about 6000 nm.

Some embodiments of the system also include a processor programmed to execute instructions to generate spectra for the detected light. In some embodiments, the processor is programmed to execute spectral fitting using proper orthogonal decomposition (POD). In some embodiments of the system, the processor is programmed to calculate percent alcohol by volume (ABV). In some embodiments of the system, the processor is programmed to calculate height of the liquid and volume of the liquid within the container.

In some embodiments of the presently-disclosed subject matter a method is provided for conducting optical measurements of a liquid in a sealed container, which involves (a) providing a device comprising a probe with fiber optic or light guiding capabilities having a leg extending downward through a bung, and an end at an upper terminus of the leg that extends upward through a bung, and a fiber optic connector for detachably coupling the end of the probe to a light source and a measurement system; (b) inserting the device through a hole defined by the container, such that the probe extends into the liquid, the container is sealed by the bung, and the fiber optic connector is accessible from the outside of the sealed container; (c) coupling the light source and the measurement system to the probe; (d) exposing the liquid to light of various wavelengths emitted from the light source; and (e) measuring the intensity of light absorbed at the various wavelengths by the liquid using the measuring system.

In some embodiments of the method, the probe is substantially U-shaped, having the leg extending downward, a base curving back up, and a second leg extending upward, wherein the end at the terminus of the first leg and a second end at the terminus of the second leg both extend through the bung, wherein the first leg includes a series of crimps, such that its diameter shrinks and expands across its length; and a second fiber optic connector for detachably coupling the second end of the probe to a light source and/or a measurement system.

In some embodiments of the method, the measurement system detects light; and further comprising a processor programmed to execute instructions to generate spectra for the detected light. In some embodiments of the method, a processor is used, which has been programmed to execute spectral fitting using proper orthogonal decomposition (POD). In some embodiments of the method, the processor is further programmed to calculate percent alcohol by volume (ABV) and/or height of the liquid and volume of the liquid within the container.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are used, and the accompanying drawings of which:

5

Figure 3A:
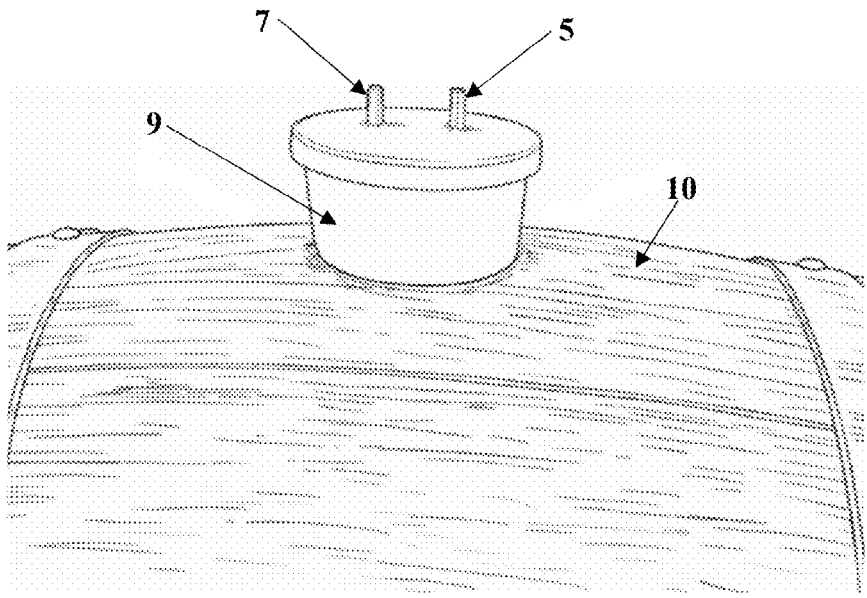
Figure 3B:
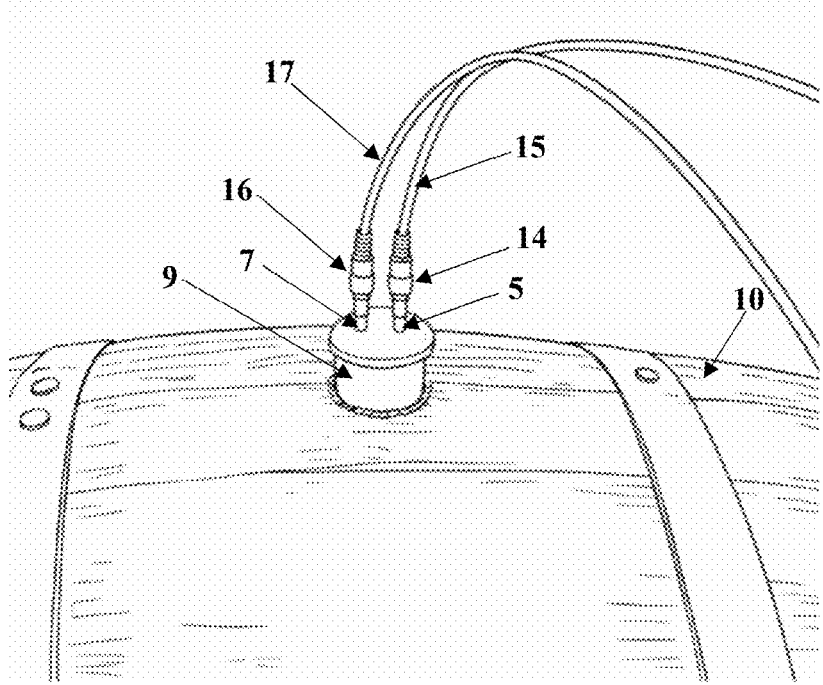
Figure 3C:
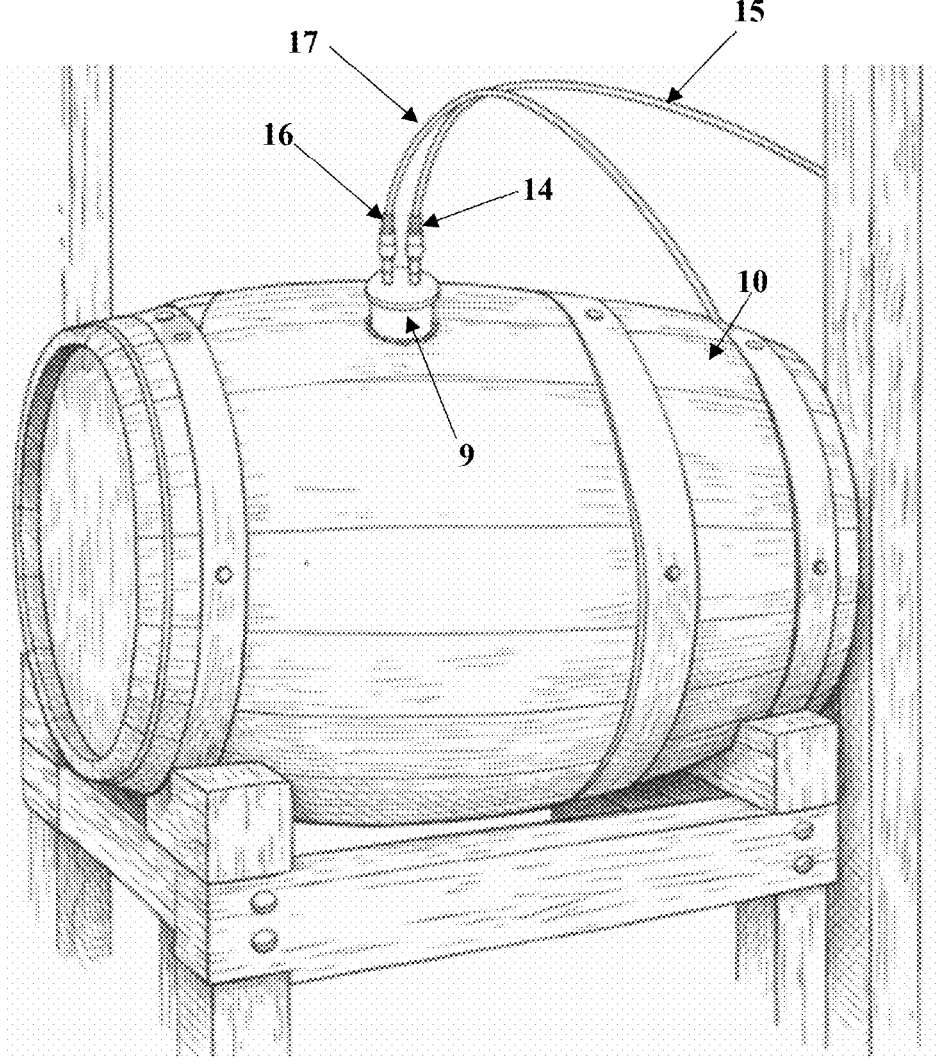

FIG. 3A-3C show an embodiment of a device inserted into a bourbon barrel.

Figure 4:
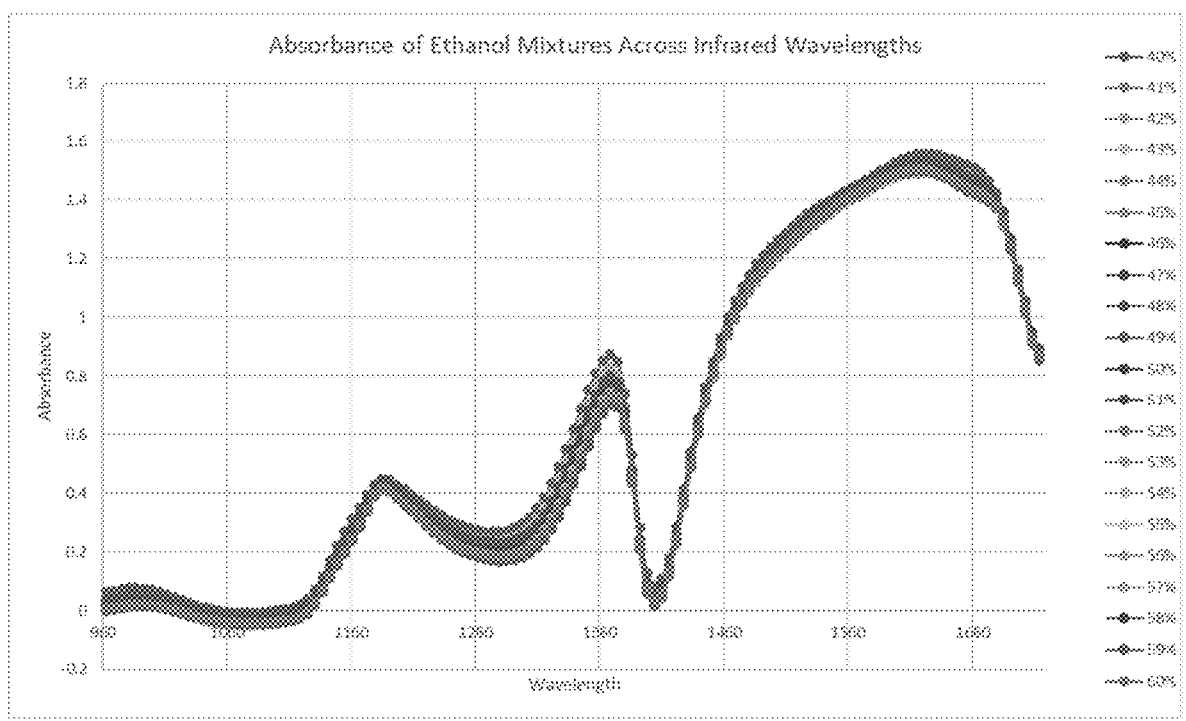

FIG. 4 includes a spectra showing absorbance of ethanol mixtures across infrared wavelengths.

Figure 5:
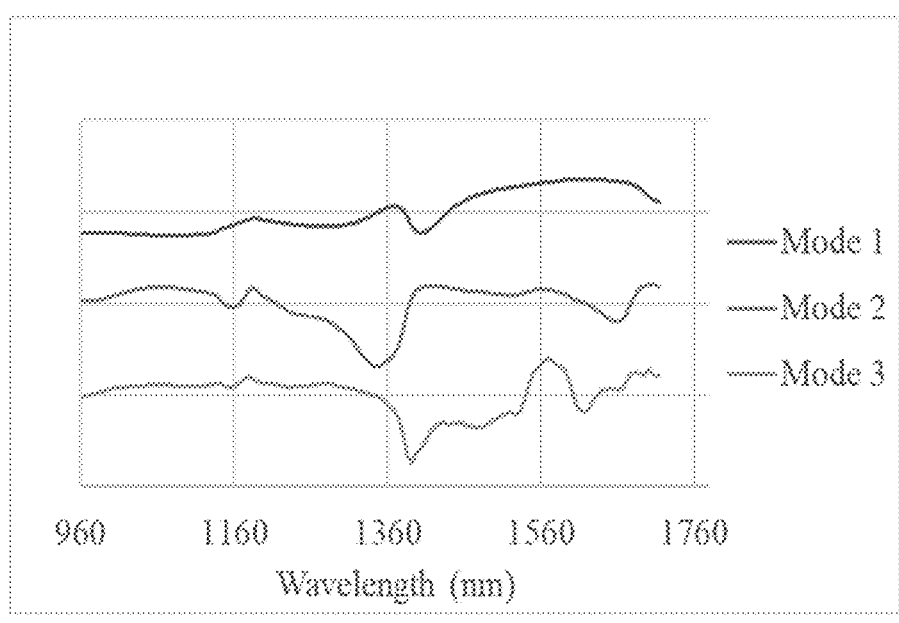

FIG. 5 includes three exemplary proper orthogonal decomposition (POD) modes representing variations observed from a training data set.

Figure 6:
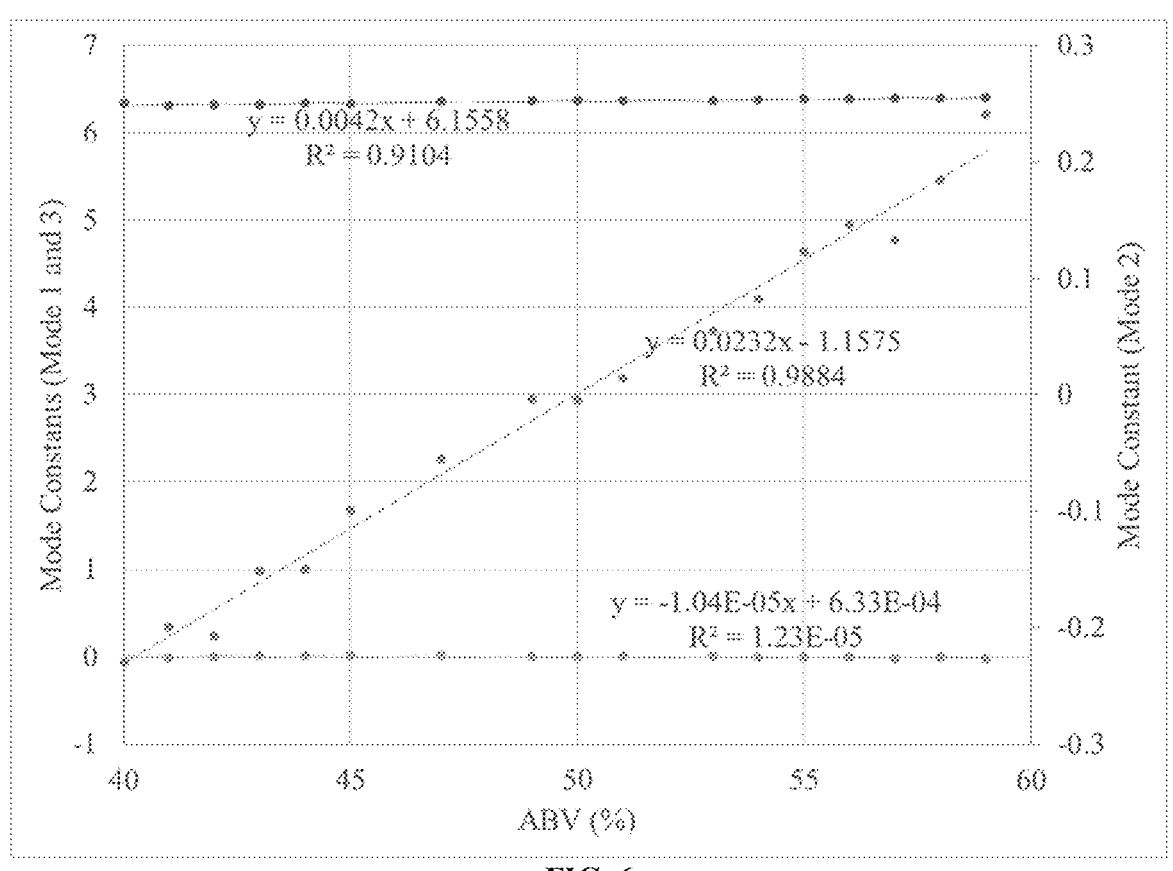

FIG. 6 includes an example of data analysis of a measured spectrum in POD, showing mode constants as a function of ABV (%).

Figure 7:
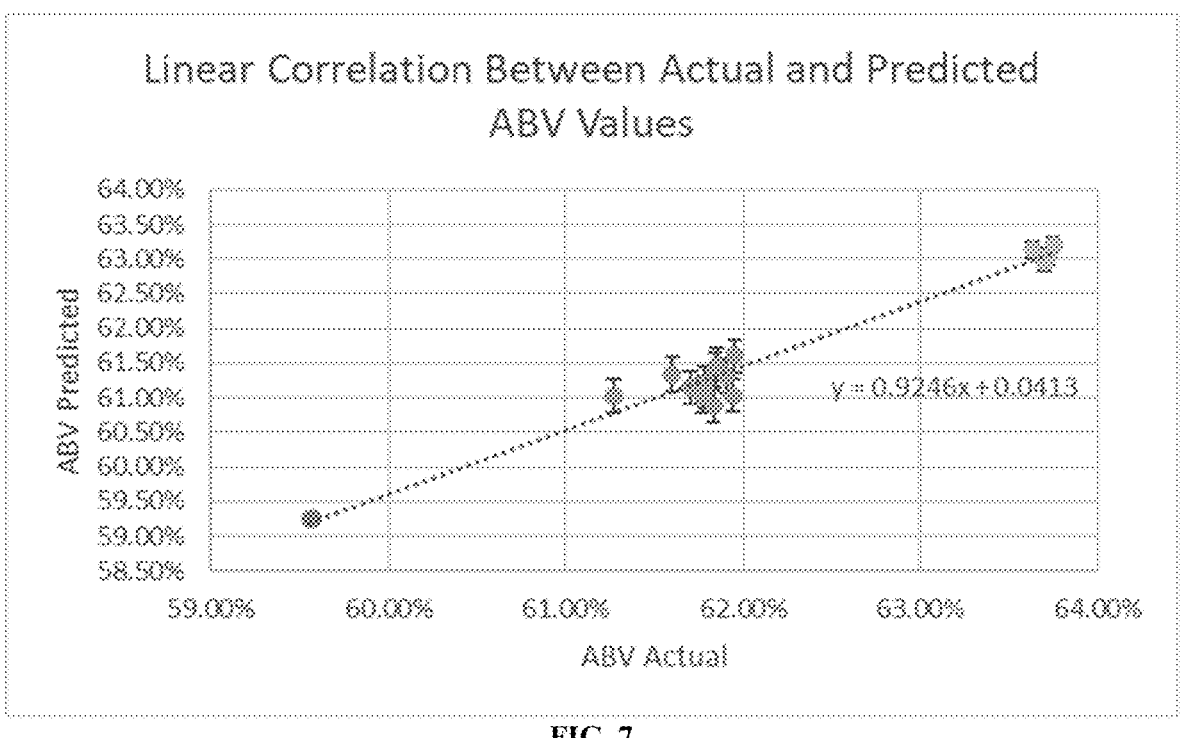

FIG. 7 includes an example of a linear correlation between actual and predicted ABV (%) values.

Figure 8:
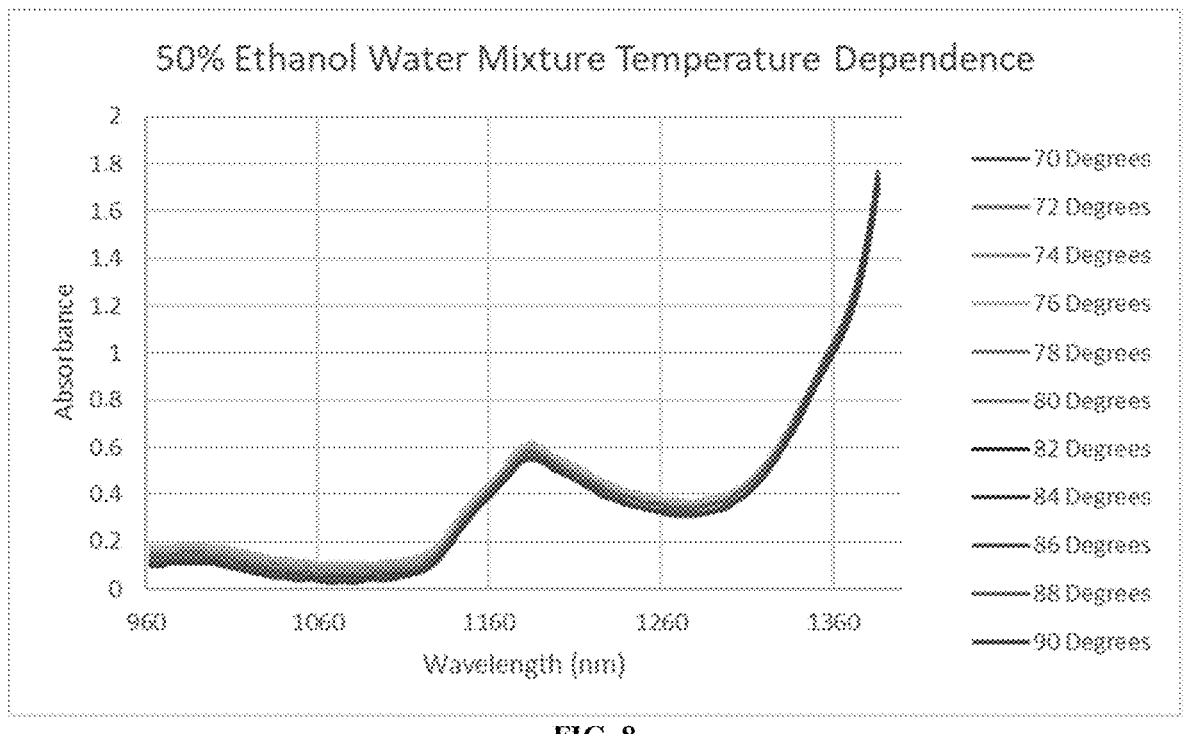

FIG. 8 includes spectra showing absorbance of 50% ethanol mixtures at various temperatures.

Figure 9:
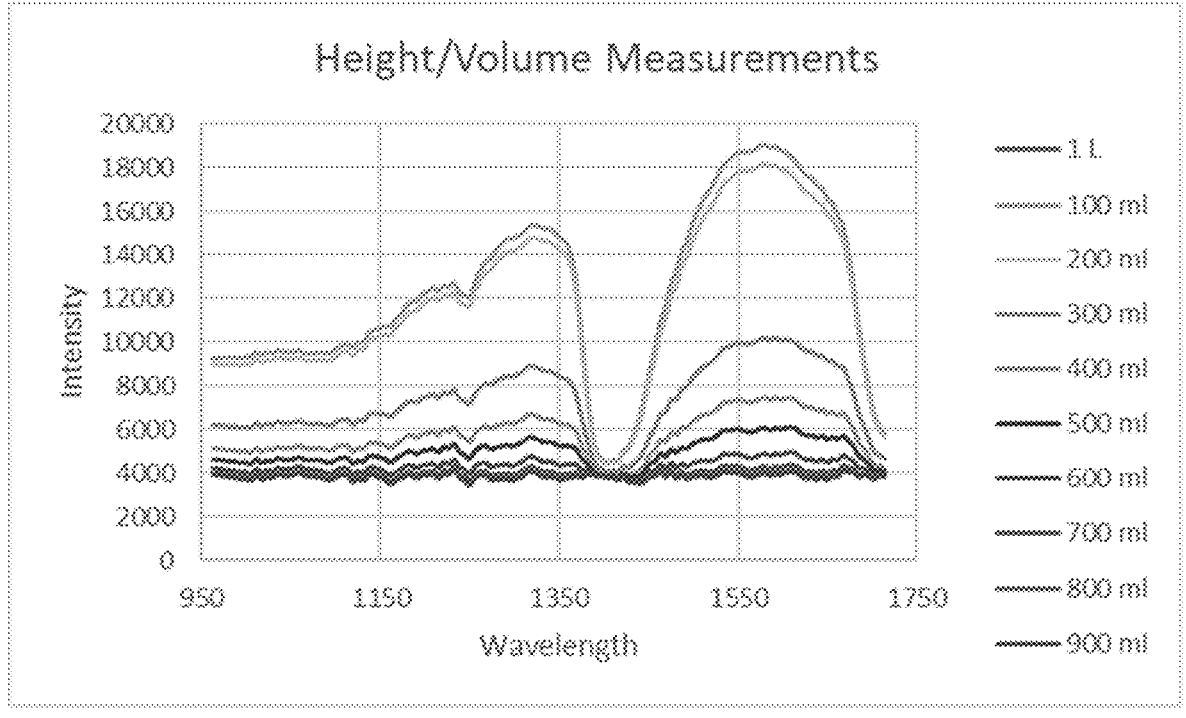

FIG. 9 includes spectra showing intensity for various liquid depths (liquid total volume) within a container.

While the disclosure is susceptible to various modifications and alternative forms, specific embodiments thereof have been shown by way of example in the drawings and are herein described below in detail. It should be understood, however, that the description of specific embodiments is not intended to limit the disclosure to cover all modifications, equivalents and alternatives falling within the spirit and scope of the disclosure as defined by the appended claims.

DESCRIPTION OF EXEMPLARY
EMBODIMENTS

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

The presently-disclosed subject matter includes devices, systems, and methods for conducting optical measurements of a liquid in a sealed container. As will be appreciated by one of ordinary skill in the art upon study of this document, such devices, systems, and methods can be useful for monitoring an alcoholic beverage being aged in a sealed container. Monitoring can include detecting such properties as alcohol by volume (ABV) (%), liquid height (volume) in the container, presence of trace chemicals and flavor components, and other physical and environmental properties of the liquid and internal environment of the sealed container.

Examples of alcoholic products that are aged and can be monitored in accordance with the presently-disclosed subject matter include, but are not limited to, whiskey/whisky, including American whiskey, bourbon, rye, scotch, Irish Whiskey, Scottish whisky, Canadian whisky, Japanese whisky, brandy, including cognac, Armagnac, Spanish brandy, rum, tequila, mescal, calvados, pisco, wine, beer, cider, mead, and sake. Examples of containers in which aging can occur include, but are not limited to, a barrel, such as a charred or uncharred wooden barrel, an opaque container, such as a glass or medal container, or any other liquid tight container.

To better understand the unique features and utility of the devices, systems, and methods of the presently-disclosed subject matter, an overview of the bourbon aging process will be described by way of an example of aging an alcoholic beverage.

For bourbon, the process begins with formulation of a mash bill, which is a carefully formulated blend of at least 51% corn, combined with other grains such as rye, barley, or wheat. This mixture is cooked and then fermented with yeast to convert the sugars into alcohol. The fermented mash or "wash" is then subjected to distillation in a copper still, where it is heated to separate the alcohol from the water and other impurities.

This distillation process is typically conducted two times to increase the purity and concentration of the alcohol. This distillation process yields a freshly-distilled sprit that is sometimes referred to as "white dog." White dog is clear and infamous for its harsh flavor. White dog is barreled and aged to become a bourbon. Under U.S. regulations, bourbon must be aged in new, charred oak containers. This is one step in the production process that distinguishes bourbon from other products, such as whiskey/whisky, which can made with previously-used barrels or non-charred barrels.

Once the white dog has been placed in the barrel, the barrel is sealed and stored for aging. Depending on the production size of the distillation batch, there may be numerous barrels needed to accommodate the overall volume. Filled barrels of a common batch are typically stored together in "rickhouse" or "rackhouse," which contain racks for tiering barrels.[1] A rickhouse can be of various sizes, depending on the quantity of barrels being aged. Regardless of the number of barrels, the design of the rickhouse should allow for air circulation and temperature variation around and within each barrel, which is important for aging process and flavor development of the bourbon.

There are a number of factors that influence the bourbon aging process, including formulation and distillation of the white dog, quality and integrity of the barrel, availability of air circulation in the rickhouse, and climate. Climate is important because temperature fluctuations in the aging environment play a significant role in how bourbon ages, as the spirit expands and contracts, drawing in and out of the oak, thereby infusing flavor, color, and complexity. For example, the hot summers and cold winters in Kentucky can provide the ideal climate for bourbon aging. The amount of time a bourbon is aged also has a significant impact on the final product.

After distillation, barreling, and storage is complete, the aging begins. During the first months and first couple of years, the bourbon starts to interact with the charred oak, extracting color, tannins, and initial flavors. At this stage, the bourbon is still considered very young and may have a sharp, raw taste with limited complexity. As the bourbon continues to age from about two (2) to four (4) years, significant flavor development occurs as the bourbon absorbs more compounds from the oak, including vanillin, lactones, and tannins. The bourbon's color deepens to a richer amber as it ages. The bourbon can be sold as straight bourbon if it has aged for at least two (2) years, although it may still have some youthful characteristics. If bourbon is labeled as "bottled in bond," it must meet additional requirements, including being aged for at least four years and bottled at 100 proof (50% ABV).

As aging continues during the period of around four (4) to eight (8) years, the bourbon often reaches a balance between the harshness of the white dog and the complexity of aged spirits. Common flavor notes include caramel, vanilla, oak, and spice. Many distillers consider this range to be optimal for standard bourbon offerings, providing a good balance of flavor and smoothness. Some bourbon products are aged for about eight (8) to twelve (12) years to bring out more complex flavors and a richer, smoother profile. Notes of dried fruit, leather, tobacco, and deep caramel often emerge. Bourbons in this age range are often marketed as premium products due to their enhanced flavor complexity.

Longer aging for about twelve (12) to twenty (20) years can lead to very complex and robust flavors. However, there is a risk of over-oaking, where the bourbon can become too woody or astringent. Bourbons aged for these longer time periods are often released as special editions or limited releases, often commanding higher prices due to their rarity and complexity. There are also bourbons product that have been aged twenty (20) years or longer. At this stage, bourbon can develop very unique and intense flavors, but only certain barrels will age gracefully without becoming overly tannic or bitter. These bourbons are rare and often sought after by collectors and connoisseurs.

As will be appreciated by one of ordinary skill in the art upon study of this document, there are a number of risks to the bourbon that can present during the aging process, which might be mitigated with appropriate monitoring. Likewise, with monitoring, opportunities may be presented to enhance the development of the bourbon during the aging process. Because there should be appropriate spacing between stored barrels to allow for air circulation, the outside each stored barrel remains accessible and can be inspected. However, the internal environment of the barrel cannot be accessed and inspected without breaching the seal of the barrel and extracting a sample of the aging bourbon. The devices, systems, and methods of the presently-disclosed subject matter provide a solution, as will become apparent upon study of this document.

Briefly, a device as disclosed herein includes a probe, a bung, and a fiber optic connector. The probe is constructed from a material having fiber optic or light guiding capabilities and extends through a hole defined by the bung, such that there is a leg of the probe extending downward from the bung, and a top end of the probe that extends upward from the bung. The top end of the probe is capped with a fiber optic connector for detachably coupling the end of the probe to a light source and/or a measurement system. The probe and bung are configured such that, when the probe is inserted into the hole defined by the bung, the hole is sealed such that liquid cannot pass through the hole once the probe has been inserted.

The devices as disclosed herein are designed to be inserted into a hole defined by a container (e.g., bourbon barrel), such that the container is sealed by the bung, and such that the device remains inserted in the sealed container for the duration of the aging process. When the device installed in the aging container, the probe extends into the liquid (e.g., white dog, bourbon), the bung seals the container, and the fiber optic connector is accessible from the outside of the container and can be used to conduct optical measurements, thereby extracting information about the interior environment of the container without breaching its seal.

Exemplary embodiments of devices, systems, and methods for conducting optical measurements of a liquid in a sealed container will be described with reference to FIG. 1 and FIG. 2. In some embodiments, the device includes a probe 2 with fiber optic capabilities having a first leg 4 extending downward, a base 8 curving back up, and a second leg 6 extending upward. With reference to FIG. 2, the first leg 4 includes a series of crimps 3, such that its diameter shrinks and expands across its length. An end 5 at the terminus of the first leg 4, and an end 7 at the terminus of the second leg 6 extend through a bung 9.

Referring back to FIG. 1, a first fiber optic connector 14 is provided for detachably coupling the end 5 of the first leg 4 via a fiber optic cable 18 to a measurement system 26, such as a spectrometer, photodetector, and/or processor. A second fiber optic connector 16 is provided for detachably coupling the end 7 of the second leg 6 via a fiber optic cable 17 to a light source 25. In some embodiments a filter 24 can also be used with the light source to select for particular wavelengths of interest. The probe 2 is inserted into the container 10 through a hold defined by the container 10, such that the probe 2 extends into the liquid (below the liquid level 12 within the container 10). The container 10 is sealed by the bung 9, and the fiber optic connectors 14, 16 are accessible from the outside of the sealed container 10, and can be coupled with and decoupled from the light source 25 and measurement system 26.

Figure 1:
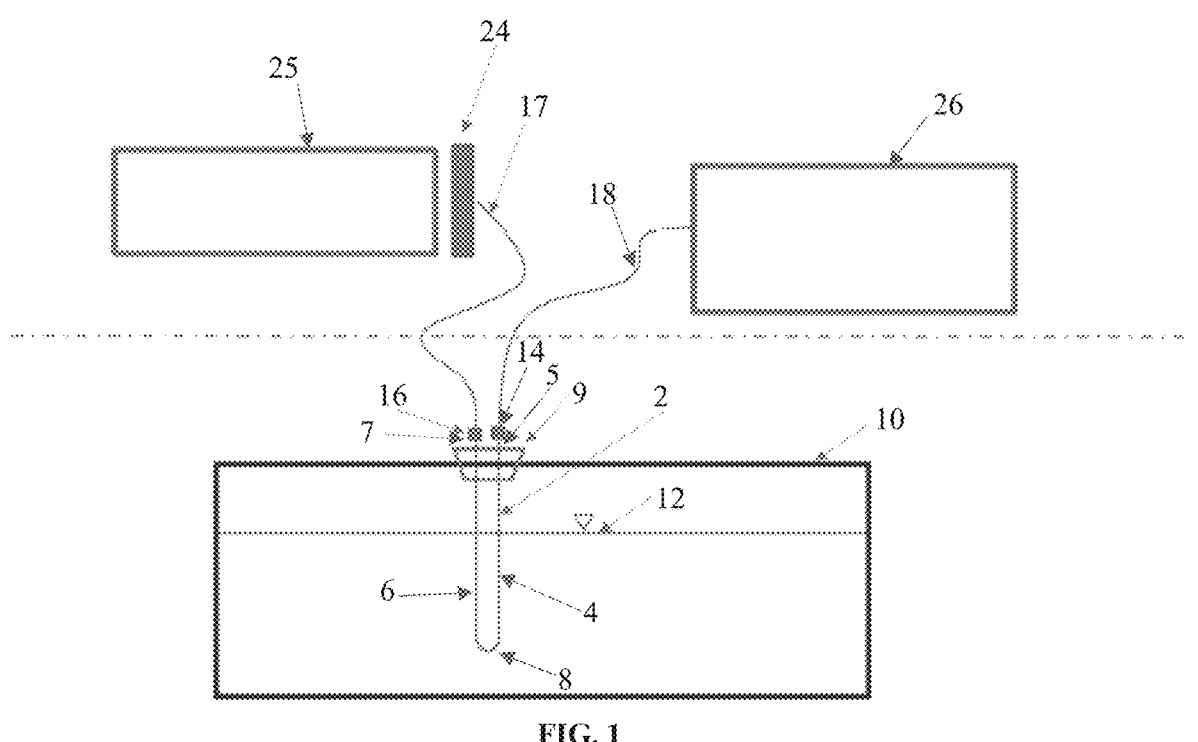
FIG. 1 shows a perspective view of a device inserted into a sealed container for conducting optical measurements of a liquid.
Figure 2:
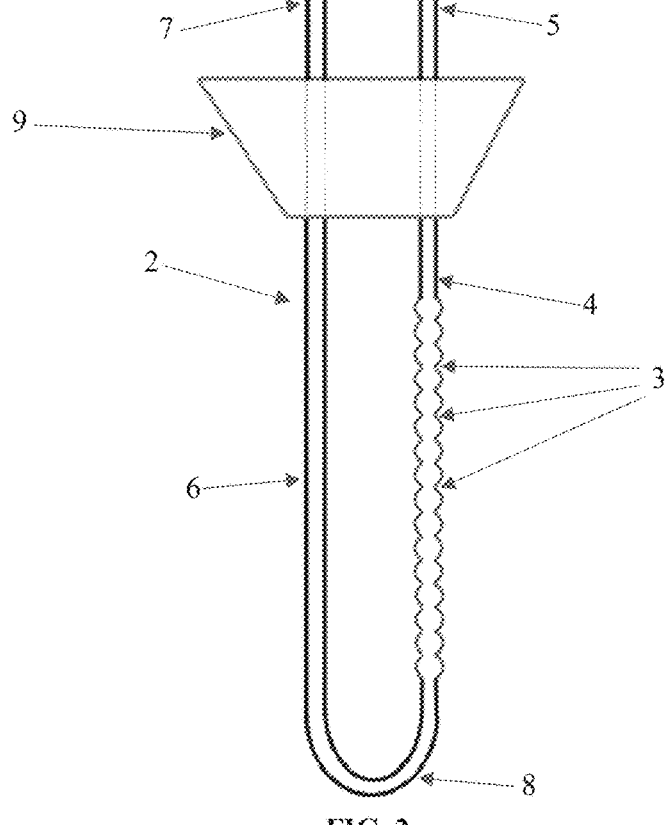
FIG. 2 shows an embodiment of a device for conducting optical measurements of a fluid in a sealed container.

As will be appreciated by one of ordinary skill in the art upon study of this document, while the embodiments depicted in FIGS. 1 and 2 include two ends 5, 7 of the probe 2 with two fiber optic connectors 14, 16 accessible from the outside of the sealed container 10, in some embodiments, there can be a single end accessible from the outside of the sealed container to which various light sources and/or other devices can be coupled and de-coupled.

In some embodiments, the light from the light source interacts with the fluid inside the sealed container without being launched from the probe. For example, in one embodiment, a reflector positioned at the end of the probe reflects the light from the light source backwards along the same probe and out of the sealed container. In such embodiments, the light either interacts with the fluid through the walls of the probe (e.g., evanescent wave absorption) or directly with fluid inside the probe (e.g., fluid that has penetrated the probe through pores in the probe/light guide). Alternatively, in some embodiments, the light from the light source is transmitted directly through the fluid within the container and is not contained within a probe during its interaction with the liquid (i.e., the light is launched from an optic outside the fluid and reflected back, with only the light contacting the fluid). For example, in one embodiment, the probe includes an embedded reflector arranged and disposed to launch the light from the light source into free space (e.g., directly through fluid within the sealed container). In such embodiments, after being launched from the end of the probe, the light is transmitted back along the same path and out of the sealed container via the same probe or via a nearby but separate collector. In another embodiment, the probe includes a porous structure that permits liquid to penetrate the inside of the tube for measurement while also limiting the intrusion of solid particulates that may exist in the liquid (i.e., the probe is in physical contact with the liquid). In such embodiments, the probe serves to limit spurious interactions with undesired features of the liquid such as particulates that could interfere with transmission while still enabling direct contact between the light and fluid.

After interacting with the fluid, the light leaving the sealed container forms a return signal including absorption features from targeted molecules in the fluid and/or other modifications such as phase delay or total transmission reduction due to differences in the index of refraction of the transversed fluid. This return signal is captured by a measurement system that detects and measures the transmitted light to determine changes that occurred due to interactions with the fluid. In some embodiments, these changes include spectrally-dependent absorption and changes in the temporal character of the light. Based upon the changes in the transmitted light various properties of the liquid within the sealed container can be determined, such as, but not limited to, volume/amount, chemical composition, particulate loading, and/or temperature. For example, in one embodiment, the measurement system measures absorption of light by the liquid to detect the total volume of liquid within the sealed container. In another embodiment, the measurement system measures absorption of light by ethanol, using different wavelengths in the transmitted light, to determine the alcohol content by volume (ABV) within the sealed container. In some embodiments, the measurement system and the light source are part of a single article that may be coupled to the guide. Additionally or alternatively, in some embodiments, the light source may be switched to measure different molecules without modifying the probe architecture.

Referring back to FIG. 1, once coupled via the fiber optic connector 16 to the light source 25, light is transmitted through the probe 2 and interacts with the liquid in the sealed container 10. Light loss through the probe 2 is increased in the presence of liquid. Accordingly, the return signal is sensitive to features of the liquid, such as its depth. Light is also preferentially absorbed at specific wavelengths based on the chemical composition of the liquid, providing a sensitivity to alcohol concentration.

With reference to FIG. 2, in some embodiments a leg 4 of the probe 2 includes a series of a series of crimps 3, such that its diameter shrinks and expands across its length. As such, the probe shape consists of some straight sections with low to zero radius of curvature that transmit the light with low loss or absorption and other sections (with crimps) provide for locally high radius of curvature. These high curvature sections lead to overall light loss related to the index of refraction of the probe and the surrounding liquid or gas. Interaction of the light remaining in the probe with the surrounding liquid or gas through evanescent wave absorption leads to preferential light loss of wavelengths associated with high absorptivity in the liquid. The probe can be made to any length and with any number of crimped sections based on expected range of liquid depth and desired resolution.

Referring back to FIG. 1, once the measurement system 26 is coupled via the fiber optic connector 14 to the probe 2, the return light is transmitted through the probe 2 to the measurement system 26. In this manner, data about the internal environment of the sealed container 10 and the liquid within can be collected without breaching the seal of the container 10.

Using bourbon aging as an example, and with reference to FIG. 3A-3C, the probe and bung 9 can be inserted into each of a series of bourbon barrels stored within a rickhouse, such that each barrel 10 is sealed by the bung 9 and the probe remains exposed to the bourbon for the duration of the aging process of the bourbon within each barrel 10. Fiber optic connector 14, 16 is provided for detachably coupling the ends 5, 7 of the probe to external devices via fiber optic cables 18, 17. Because of the spacing between stored barrels to allow for air circulation and inspection, the end(s) of the probe with fiber optic connector(s) remains accessible from the outside of each barrel.

Data collection for the entire rickhouse can occur by coupling a light source and measurement system to the probe in a first barrel, then decoupling and moving to the next barrel, until data for all of the barrels in the rickhouse have been collected. As will be appreciated, a particular barrel can be tied to a particular data set using various mechanisms, including but not limited to, barcode scanning, quick response code scanning, radio-frequency identification tags, and near field communication tags. The light source and measurement system, including desired processing equipment such as a laptop computer, could be packed together to allow for ease of transport through the rickhouse, e.g., in a backpack from which fiber optic cables extend for ready coupling to and decoupling from the fiber optic connectors exposed on the outside of each barrel.

In some embodiments of the present-disclosed subject matter, a device is provided, which includes a probe with fiber optic capabilities having a leg extending downward through a bung, the leg including a series of crimps, such that its diameter shrinks and expands across its length and an end at an upper terminus of the leg that extends upward through the bung. The device can further include a fiber optic connector for detachably coupling the end of the probe to a light source and/or a measurement system.

In some embodiments, the probe is substantially U-shaped, wherein the leg extends downward, a base curves back up, and a second leg extends upward, and wherein the end at the upper terminus of the first leg and a second end at the upper terminus of the second leg both extend through the bung. The device can further include a second fiber optic connector for detachably coupling the second end of the probe to a light source and/or a measurement system.

As will be appreciated by one of ordinary skill in the art upon study of this document, consideration should be given to ensuring efficient light transmission and durability when selecting an appropriate material for the probe with fiber optic capabilities. For example, glass is an appropriate material due to its excellent optical clarity and low attenuation, making it useful for high-precision measurements. Silicone elastomers are also suitable for fiber optic applications, offering flexibility, biocompatibility, and resistance to harsh chemical environments. In some embodiments, materials such as sapphire, calcium fluoride, or magnesium fluoride can be useful. The material is selected to provide the necessary light guiding properties at any required wavelengths to maintain the integrity and performance of fiber optic probes in alcohol-containing liquid, ensuring accurate data collection and long-term reliability. Such probes can be designed to be solid or could be a bare fiber optic or a permeable fiber optic, including one that is hollow.

In some cases, due to their beneficial properties, it can be desirable to select a material and configuration for the probe that is delicate. In this regard, in some embodiments, the device can also include a protective sleeve surrounding the probe. As will be appreciated by one of ordinary skill in the art upon study of this document, the protective sleeve can be used to avoid damage to the probe, particularly where a relatively fragile material is used when constructing the probe. Furthermore, as will be appreciated, the protective sleeve is designed such that contact between the probe and the liquid is maintained. For example, the sleeve can be attached to the bung, while being open at the base and/or having a number of permeations to allow for continuous contact between the liquid and the probe, while also providing a protective boundary around the probe. The protection can serve to avoid damage to the probe, for example, at the time that it is inserted into the container at such time as the container is sealed with the bung.

In some embodiments, the device further includes a container, wherein the bung is placed such that the legs and base of the probe extend into the container, the bung seals the container, and the fiber optic connectors are accessible on the outside of the sealed container, accessible for coupling/decoupling external devices. As will be appreciated by one of ordinary skill in the art, various fiber optic connectors and fiber optic cables are known in the art and can be selected for use in accordance with the presently-disclosed subject matter for connecting the probe to light source and/or measurement systems. Examples of fiber optic connectors include, but are not limited to subscriber connector (SC), lucent connector (LC), straight tip (ST), ferrule connector (FC), and multi-fiber push-on/pull-off (MTP/MPO). Examples of fiber optic cables include, but are not limited to single-mode fiber (SMF), multi-mode fiber (MMF), armored fiber cable (AFC), ribbon fiber cable (RFC), simplex and duplex fiber cable.

In some embodiments of the present-disclosed subject matter, a system is provided, which includes a device as disclosed herein, a light source, and a measuring system.

As will be appreciated by one of ordinary skill in the art upon study of this document, various light sources are known and can be selected for use in connection with the presently-disclosed subject matter. The light source and range of emission wavelengths can be selected with consideration, for example, to features of the liquid (e.g., alcohol content, trace chemicals and flavor components, etc.) that are desired to be measured and the materials of the probe (e.g., sapphire, calcium fluoride, or magnesium fluoride, etc.). Examples include, but are not limited to, a broadband lamp, an external optical system, lasers, including tunable lasers such as tunable infrared lasers, light emitting diodes, non-lasing narrow band diode light sources, and multiple light sources collected into one fiber. In some embodiments, the light source emits light having wavelengths of about 400 nm to about 6000 nm. In some embodiments, the light source emits light having wavelengths of about 400 nm to about 2500 nm. In some embodiments, the light source emits light having wavelengths of about 3000 nm to about 6000 nm.

As will also be appreciated by one of ordinary skill in the art upon study of this document, various measurement systems are known and can be used in accordance with the presently-disclosed subject matter, depending on the properties being monitored. Examples include, but are not limited to, high resolution spectrometer, optical filters, photodiodes, other optical measurement systems, and computers having processors.

In some embodiments, the measuring system(s) include a spectrometer or photodetector for detecting light. The system may include optical filters. Various spectrometer or photodetector are known in the art and many commercially available, and can be appropriately selected by one of ordinary skill in the art upon review of this document. The spectrometer or photodetector and range of detected wavelengths can be selected with consideration, for example, to features of the liquid (e.g., alcohol content, trace chemicals and flavor components, etc.) that are desired to be measured and the materials of the probe (e.g., sapphire, calcium fluoride, or magnesium fluoride, etc.). In some embodiments, the measuring system(s) include a spectrometer or photodetector for detecting light having wavelengths of about 400 nm to about 6000 nm. In some embodiments, the measuring system(s) include a spectrometer or photodetector for detecting light having wavelengths of about 900 nm to about 1700 nm. In some embodiments, the measuring system(s) include a spectrometer or photodetector for detecting light having wavelengths of about 1100 nm to about 1600 nm. In some embodiments, the measuring system(s) include a spectrometer or photodetector for detecting light having wavelengths of about 1300 to about 1400 nm. In some embodiments, the light source emits light having wavelengths of about 3000 nm to about 6000 nm.

In some embodiments, the system includes a processor programmed to execute instructions to generate spectra for the detected light. In some embodiments, the system includes a processor programmed to execute spectral fitting using proper orthogonal decomposition (POD). In some embodiments, the processor is further programmed to calculate percent alcohol by volume (ABV). In some embodiments, the processor is programmed to calculate height of the liquid and volume of the liquid within the container. In some embodiments, the processor is programmed to calculate presence of trace chemicals and flavor components, and other physical and environmental properties of the liquid and internal environment of the sealed container In some embodiments of the present-disclosed subject matter, a method is provided for using a device and/or system as disclosed herein. In some embodiments, the method includes (a) providing a device as disclosed herein, (b) inserting the device through a hole defined by container, such that the probe extends into the liquid, the container is sealed by the bung, and the fiber optic connector is accessible from the outside of the sealed container, (c) coupling the light source and the measurement system to the probe, (d) exposing the liquid to light of various wavelengths emitted from the light source, and (e) measuring the intensity of light absorbed at the various wavelengths by the liquid using the measuring system.

In some embodiments, the method makes use of a processor programmed to execute instructions to generate spectra for the detected light. In some embodiments, the processor is programmed to execute spectral fitting using proper orthogonal decomposition (POD). In some embodiments, the processor is programmed to calculate percent alcohol by volume (ABV). In some embodiments, the processor is programmed to calculate height of the liquid and volume of the liquid within the container. In some embodiments, the processor is programmed to calculate presence of trace chemicals and flavor components, and other physical and environmental properties of the liquid and internal environment of the sealed container With regard to assessment of ABV, reference is made to FIG. 4. Various known ABV (%) fraction mixtures were prepared, ranging from 40% to 60%. Using a device in accordance with the presently-disclosed subject matter, sample measurements were taken and return spectra versus wavelength for the mixtures were generated. FIG. 4 includes such spectra. Some regions of the spectra are insensitive to ABV (e.g., around 1200 nm) while other regions have high sensitivity to ABV (e.g., around 1360 nm). As disclosed herein, embodiments of the analysis of measured spectra make use of the entire spectrum to determine ABV.

As disclosed herein, in some embodiments, proper orthogonal decomposition (POD) is used to execute spectral fitting. POD is a powerful mathematical technique used for dimensionality reduction and feature extraction in various fields, including signal processing and spectral fitting. When applied to spectral fitting, POD helps to analyze and decompose complex spectra into a set of orthogonal basis functions, making it easier to identify and quantify the underlying components.

POD is a linear decomposition, like Fourier decomposition, where the modes are determined directly from the data to be decomposed.[2] Briefly, POD for spectral fitting generally involves the following. Data collection and initial processing is conducted, including collection of desired spectra. Initial processing of the spectral data can be conducting, such as normalization, to provide consistency across a dataset. The spectral data is arranged into a data matrix with dimensions defined by the number of spectra and the number of wavelengths or frequencies. Orthogonal decomposition is applied and the most significant modes are selected. These significant modes capture the most variance in the spectral data and are used to represent the dominant features. A procedure, referred to herein as "renormalization," is performed to reduce crosstalk in the decomposed spectra.[3] The original spectral data is projected onto the selected POD modes to obtain the coefficients that describe how much of each mode is present in the original spectra. The selected modes and their coefficients are used to reconstruct the spectra. This reduces noise and highlights the important spectral features. For an example for use in connection with the presently-disclosed subject matter, the data (OD) as a function of wavelength (j) and other experimental parameters (t) is represented by a sum of constants (a) multiplied by mode shapes (v).

$$OD_j^t = \sum_{i=1}^{M} a_i^t v_i^j$$

With reference to the examples in FIG. 4 and FIG. 5, proper orthogonal decomposition (POD) can be used to determine spectral modes that best represent the variations observed from a training data set, consisting of mixtures with known ABV (%) and liquid depth (volume) within a container. An example of three POD modes from such data are shown in FIG. 5. These are shifted vertically in the graph. Mode 1 represents the average shape of the measured spectra as seen in FIG. 4. Mode 2 represents the departures from this average spectrum resulting from changes in ABV (%). Note the region around 1200 nm that is insensitive to ABV is approximately zero in mode 2, whereas the mode has a minimum value near 1360 where the spectrum is most sensitive to ABV. This mode shape captures the impact of ABV on the spectrum at all wavelengths. Similar modes can be used for depth and other measurements of interest by incorporating broader training data sets.

With reference to the example in FIG. 6, data analysis of a measured spectrum in POD is accomplished by decomposing the measurement into the pre-determined modes. The mode constants represent the weight of that mode in the individual measurement. Optimized modes developed from training data shown in FIG. 6 indicate that mode 2 provides a linear correlation to ABV. The mode constant can be calibrated from known standards for a given probe to determine ABV.

With reference to the example in FIG. 7, Measurements were conducted in bourbon samples aged in a barrel from 0.5 year to 25 years to establish efficacy for the measurement. The known bourbon ABV (%) determined from industry standard extractive sampling devices was compared to the in-situ measurement as disclosed herein. The measurement is accurate to within 0.15% (0.3 proof) over the range of ABV values observed in barrels.

With reference to the example in FIG. 8, measurements of spectra in 50% ABV mixtures as a function of liquid temperature show small variations. POD analysis can be used to extract temperature simultaneous to ABV and liquid height (volume) measurements.

With reference to FIG. 9, measurements of raw spectra versus liquid height (liquid total volume) were obtained. Changes in return signal are due to increased light loss in the presence of more (deeper) liquid. POD modes correlated to depth were also computed and determined depth with a spatial resolution of 10 mm.

As will be appreciated by one of ordinary skill in the art upon study of this document, while embodiments have been described herein in connection with their use with aging an alcoholic beverage in a closed container, the disclosed devices, systems, and methods have utility in other contexts. Examples of context in which the disclosed devices, systems, and methods could be used to monitor properties of a liquid or gas within a closed container include, but are not limited to, the following.

When performing certain chemical reactions, it can be useful to monitor properties of reactants and products within a closed reactor to optimize yield and safety. For pharmaceutical manufacturing, including sterilization, it can be useful to monitor properties inside sterilization equipment to ensure proper sterilization of medical instruments and pharmaceuticals. It can also be useful to monitor properties of gases and liquids within distillation columns and reactors to control the production of fuels, lubricants, and other chemicals. In connection with stability and drug storage, it can also be useful to monitor properties inside storage containers to ensure the stability and potency of pharmaceuticals over time.

In connection with food and beverage production, including non-alcoholic or low-alcoholic beverage (i.e., less than about 2%, less than about 1%, less than about 0.5%, or about 0% ABV) and non-aged alcoholic beverage production, it can be useful to monitor properties inside fermentation tanks for producing products like kambucha, yogurt, and sauerkraut to ensure consistent quality and safety.

In connection with environmental monitoring, it can be useful to monitor properties inside emission control devices to ensure compliance with environmental regulations, including regulations in connection with particular pollutants.

In connection with semiconductor manufacturing, it can be useful to monitor properties inside chemical vapor deposition (CVD) chambers to ensure the uniform deposition of thin films.

In connection with aerospace engineering, it can be useful to monitor properties inside fuel tanks to ensure safety and efficiency during flight.

In connection with cryogenics, it can be useful to monitor properties inside containers storing cryogenic fluids like liquid nitrogen or helium to prevent hazards and maintain desired conditions.

In connection with battery manufacturing and storage, such as with lithium-ion batteries, it can be useful to monitor properties inside battery cells to prevent overheating, optimize performance, and ensure safety.

While the terms used herein are believed to be well understood by those of ordinary skill in the art, certain definitions are set forth to facilitate explanation of the presently-disclosed subject matter.

Unless defined otherwise, all technical and scientific terms used herein have the same meaning as is commonly understood by one of skill in the art to which the invention(s) belong.

Although any methods, devices, and materials similar or equivalent to those described herein can be used in the practice or testing of the presently-disclosed subject matter, representative methods, devices, and materials are described herein.

The present application can "comprise" (open ended) or "consist essentially of" the components of the present invention as well as other ingredients or elements described herein. As used herein, "comprising" is open ended and means the elements recited, or their equivalent in structure or function, plus any other element or elements which are not recited. The terms "having" and "including" are also to be construed as open ended unless the context suggests otherwise.

Following long-standing patent law convention, the terms "a," "an," and "the" refer to "one or more" when used in this application, including the claims. Thus, for example, reference to "a liquid" includes a plurality of liquids, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments±20%, in some embodiments±10%, in some embodiments±5%, in some embodiments±1%, in some embodiments±0.5%, in some embodiments±0.1%, in some embodiments±0.01%, and in some embodiments±0.001% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, "optional" or "optionally" means that the subsequently described event or circumstance does or does not occur and that the description includes instances where said event or circumstance occurs and instances where it does not. For example, an optionally variant portion means that the portion is variant or non-variant.

All publications, patents, and patent applications mentioned in this specification are herein incorporated by reference to the same extent as if each individual publication, patent, or patent application was specifically and individually indicated to be incorporated by reference, including the references set forth in the following list:

REFERENCES

1. Reissued U.S. Pat. No. 9,175 to Frederick Stitzel for "Rack for Tiering Barrels," Apr. 27, 1880.
2. Rathinam, M., L. R. Petzold, "A New Look at Proper Orthogonal Decomposition," SIAM *J. Numer. Anal.* 41 (2003) 1893-1925.
3. Kim, H. N., M. P. Hawron, W. Hassan, E. H. Jordan, M. W. Renfro, "Contaminant identification during laser cleaning of thermal barrier coatings," *Surface & Coatings Tech.* 270 (2015) 86-94.

It will be understood that various details of the presently disclosed subject matter can be changed without departing from the scope of the subject matter disclosed herein.

Furthermore, the foregoing description is for the purpose of illustration only, and not for the purpose of limitation.

What is claimed is:

1. A system for conducting optical measurements of a liquid in a sealed container, comprising:
   a device comprising
      a probe with fiber optic or light guiding capabilities having
         a leg extending downward through a bung, the leg including a series of crimps, such that its diameter shrinks and expands across its length; and
         an end at an upper terminus of the leg that extends upward through the bung; and
      a fiber optic connector for detachably coupling the end of the probe to a light source and/or a measurement system;
      a sealed container, wherein the bung is placed such that the probe extends into the sealed container, and the fiber optic connector is accessible on the outside of the sealed container;
   a light source; and
   a measurement system for measuring the intensity of transmitted light as a function of wavelength.

2. The system of claim 1, wherein the probe is substantially U-shaped, having the leg extending downward, a base curving back up, and a second leg extending upward, wherein the end at the terminus of the first leg and a second end at the terminus of the second leg both extend upward through the bung; and a second fiber optic connector for detachably coupling the second end of the probe to a light source and/or a measurement system.

3. The system of claim 1, wherein the light source emits light having wavelengths of about 400 nm to about 6000 nm, about 400 nm to about 2500 nm, or about 3000 nm to about 6000 nm.

4. The system of claim 1, wherein the measurement system is a spectrometer or photodetector.

5. The system of claim 1, wherein the measurement system detects light having wavelengths of about 400 nm to about 6000 nm, about 900 nm to about 1700 nm, about 1100 nm to about 1600 nm, 1300 to about 1400 nm or about 3000 nm to about 6000 nm.

6. The system of claim 5, and further comprising a processor programmed to execute instructions to generate spectra for the detected light.

7. The system of claim 6, and further comprising a processor programmed to execute spectral fitting using proper orthogonal decomposition (POD).

8. The system of claim 7, wherein the processor is further programmed to calculate percent alcohol by volume (ABV).

9. The system of claim 7, wherein the processor is further programmed to calculate height of the liquid and volume of the liquid within the container.

10. A method of conducting optical measurements of a liquid in a sealed container, comprising:
   (a) providing a device comprising
      a probe with fiber optic or light guiding capabilities having
         a leg extending downward through a bung, the leg including a series of crimps, such that its diameter shrinks and expands across its length; and
         an end at an upper terminus of the leg that extends upward through a bung; and

US 12,663,407 B2

17 a fiber optic connector for detachably coupling the end of the probe to a light source and a measurement system;

(b) inserting the device through a hole defined by the container, such that the probe extends into the liquid, the container is sealed by the bung, and the fiber optic connector is accessible from the outside of the sealed container;

(c) coupling the light source and the measurement system to the probe;

(d) exposing the liquid to light of various wavelengths emitted from the light source; and (e) measuring the intensity of light absorbed at the various wavelengths by the liquid using the measuring system.

11. The method of claim 10, wherein the probe is substantially U-shaped, having the leg extending downward, a base curving back up, and a second leg extending upward, wherein

18 the end at the terminus of the first leg and a second end at the terminus of the second leg both extend through the bung; and a second fiber optic connector for detachably coupling the second end of the probe to a light source and/or a measurement system.

12. The method of claim 10, wherein the measurement system detects light; and further comprising a processor programmed to execute instructions to generate spectra for the detected light.

13. The method of claim 12, and further comprising a processor programmed to execute spectral fitting using proper orthogonal decomposition (POD).

14. The method of claim 13, wherein the processor is further programmed to calculate percent alcohol by volume (ABV) and/or height of the liquid and volume of the liquid within the container.

\* \* \* \* \*